United States Patent
Bailly et al.

(10) Patent No.: US 10,159,555 B2
(45) Date of Patent: Dec. 25, 2018

(54) PACKAGING FOR A HERNIA REPAIR DEVICE

(71) Applicant: Sofradim Production, Trévoux (FR)

(72) Inventors: Pierre Bailly, Caluire-et-Cuire (FR); Thomas Vial, Villefranche-sur-Saône (FR)

(73) Assignee: Sofradim Production, Trevoux (FR)

( * ) Notice: Subject to any disclaimer, the term of this patent is extended or adjusted under 35 U.S.C. 154(b) by 788 days.

(21) Appl. No.: 14/421,275

(22) PCT Filed: Sep. 27, 2013

(86) PCT No.: PCT/IB2013/002844
§ 371 (c)(1),
(2) Date: Feb. 12, 2015

(87) PCT Pub. No.: WO2014/049446
PCT Pub. Date: Apr. 3, 2014

(65) Prior Publication Data
US 2015/0209129 A1    Jul. 30, 2015

Related U.S. Application Data

(60) Provisional application No. 61/706,912, filed on Sep. 28, 2012.

(51) Int. Cl.
*A61F 2/00*      (2006.01)
*B65D 25/20*     (2006.01)
(Continued)

(52) U.S. Cl.
CPC .......... *A61F 2/0095* (2013.01); *A61F 2/0063* (2013.01); *B65D 17/4011* (2018.01);
(Continued)

(58) Field of Classification Search
CPC ... A61F 2/0095; A61F 2/0063; B65D 17/163; B65D 25/025; B65D 65/38; B65D 81/18; A61B 50/33
(Continued)

(56) References Cited

U.S. PATENT DOCUMENTS 1,187,158 A   6/1916   Mcginley
3,118,294 A   1/1964   Van Laethem
(Continued)

FOREIGN PATENT DOCUMENTS

CA    1317836 C    5/1993
DE    19544162 C1  4/1997
(Continued)

OTHER PUBLICATIONS

Australian Examination Report dated May 24, 2017 in corresponding Australian Patent Application No. 2013322268, 3 pages.
(Continued)

*Primary Examiner* — Ernesto Grano (57) ABSTRACT

A packaging member for a hernia repair device including a surgical mesh and at least one grasping member. The packaging member includes a central portion configured to receive the surgical mesh, at least one recessed track section configured to receive the at least one grasping member, and a knob extending into the at least one recessed track section. The knob is configured to retain the at least one grasping member within the at least one recessed track section.

20 Claims, 6 Drawing Sheets

(51) Int. Cl.
  *B65D 65/38* (2006.01)
  *B65D 81/18* (2006.01)
  *B65D 17/28* (2006.01)
(52) U.S. Cl.
  CPC ........... *B65D 25/205* (2013.01); *B65D 65/38* (2013.01); *B65D 81/18* (2013.01)
(58) Field of Classification Search
  USPC ........................................................ 206/440
  See application file for complete search history.

(56) References Cited

U.S. PATENT DOCUMENTS

| | | | |
|---|---|---|---|
| 3,124,136 A | 3/1964 | Usher | |
| 3,272,204 A | 9/1966 | Charles et al. | |
| 3,276,448 A | 10/1966 | Usher | |
| 3,320,649 A | 5/1967 | Naimer | |
| 3,364,200 A | 1/1968 | Ashton et al. | |
| 3,570,482 A | 3/1971 | Emoto et al. | |
| 3,770,119 A * | 11/1973 | Hultberg | A61B 50/30 206/439 |
| 4,006,747 A | 2/1977 | Kronenthal et al. | |
| 4,060,081 A | 11/1977 | Yannas et al. | |
| 4,173,131 A | 11/1979 | Pendergrass et al. | |
| 4,193,137 A | 3/1980 | Heck | |
| 4,216,860 A * | 8/1980 | Heimann | A61M 25/002 206/364 |
| 4,248,064 A | 2/1981 | Odham | |
| 4,279,344 A | 7/1981 | Holloway, Jr. | |
| 4,294,241 A | 10/1981 | Miyata | |
| 4,307,717 A | 12/1981 | Hymes et al. | |
| 4,338,800 A | 7/1982 | Matsuda | |
| 4,476,697 A | 10/1984 | Schafer et al. | |
| 4,487,865 A | 12/1984 | Balazs et al. | |
| 4,500,676 A | 2/1985 | Balazs et al. | |
| 4,511,653 A | 4/1985 | Play et al. | |
| 4,527,404 A | 7/1985 | Nakagaki et al. | |
| 4,586,930 A * | 5/1986 | Kelman | A61F 2/16 206/438 |
| 4,591,501 A | 5/1986 | Cioca | |
| 4,597,762 A | 7/1986 | Walter et al. | |
| 4,603,695 A | 8/1986 | Ikada et al. | |
| 4,631,932 A | 12/1986 | Sommers | |
| 4,670,014 A | 6/1987 | Huc et al. | |
| 4,709,562 A | 12/1987 | Matsuda | |
| 4,748,078 A | 5/1988 | Doi et al. | |
| 4,759,354 A | 7/1988 | Quarfoot | |
| 4,769,038 A | 9/1988 | Bendavid et al. | |
| 4,796,603 A | 1/1989 | Dahlke et al. | |
| 4,813,942 A | 3/1989 | Alvarez | |
| 4,841,962 A | 6/1989 | Berg et al. | |
| 4,854,316 A | 8/1989 | Davis | |
| 4,925,294 A | 5/1990 | Geshwind et al. | |
| 4,931,546 A | 6/1990 | Tardy et al. | |
| 4,942,875 A | 7/1990 | Hlavacek et al. | |
| 4,948,540 A | 8/1990 | Nigam | |
| 4,950,483 A | 8/1990 | Ksander et al. | |
| 4,970,298 A | 11/1990 | Silver et al. | |
| 5,002,551 A | 3/1991 | Linsky et al. | |
| 5,147,374 A | 9/1992 | Fernandez | |
| 5,162,430 A | 11/1992 | Rhee et al. | |
| 5,171,273 A | 12/1992 | Silver et al. | |
| 5,176,692 A | 1/1993 | Wilk et al. | |
| 5,179,818 A * | 1/1993 | Kalinski | A61B 17/06133 53/409 |
| 5,192,301 A | 3/1993 | Kamiya et al. | |
| 5,196,185 A | 3/1993 | Silver et al. | |
| 5,201,745 A | 4/1993 | Tayot et al. | |
| 5,201,764 A | 4/1993 | Kelman et al. | |
| 5,206,028 A | 4/1993 | Li | |
| 5,217,493 A | 6/1993 | Raad et al. | |
| 5,219,077 A * | 6/1993 | Transue | A61F 2/0063 206/438 |
| 5,249,682 A * | 10/1993 | Transue | A61F 2/0063 206/438 |
| 5,254,133 A | 10/1993 | Seid | |
| 5,256,418 A | 10/1993 | Kemp et al. | |
| 5,263,983 A | 11/1993 | Yoshizato et al. | |
| 5,304,595 A | 4/1994 | Rhee et al. | |
| 5,306,500 A | 4/1994 | Rhee et al. | |
| 5,324,775 A | 6/1994 | Rhee et al. | |
| 5,328,955 A | 7/1994 | Rhee et al. | |
| 5,334,527 A | 8/1994 | Brysk | |
| 5,339,657 A | 8/1994 | McMurray | |
| 5,350,583 A | 9/1994 | Yoshizato et al. | |
| 5,356,432 A | 10/1994 | Rutkow et al. | |
| 5,368,549 A | 11/1994 | McVicker | |
| 5,368,602 A * | 11/1994 | de la Torre | A61B 17/0057 602/44 |
| 5,376,375 A | 12/1994 | Rhee et al. | |
| 5,376,376 A | 12/1994 | Li | |
| 5,392,918 A * | 2/1995 | Harrison | A61M 25/002 206/364 |
| 5,397,331 A | 3/1995 | Himpens et al. | |
| 5,399,361 A | 3/1995 | Song et al. | |
| 5,413,791 A | 5/1995 | Rhee et al. | |
| 5,425,740 A | 6/1995 | Hutchinson, Jr. | |
| 5,428,022 A | 6/1995 | Palefsky et al. | |
| 5,433,996 A | 7/1995 | Kranzler et al. | |
| 5,441,491 A | 8/1995 | Verschoor et al. | |
| 5,441,508 A | 8/1995 | Gazielly et al. | |
| 5,456,693 A | 10/1995 | Conston et al. | |
| 5,456,711 A | 10/1995 | Hudson | |
| 5,466,462 A | 11/1995 | Rosenthal et al. | |
| 5,480,644 A | 1/1996 | Freed | |
| 5,487,895 A | 1/1996 | Dapper et al. | |
| 5,490,984 A | 2/1996 | Freed | |
| 5,512,291 A | 4/1996 | Li | |
| 5,512,301 A | 4/1996 | Song et al. | |
| 5,514,181 A | 5/1996 | Light et al. | |
| 5,522,840 A | 6/1996 | Krajicek | |
| 5,523,348 A | 6/1996 | Rhee et al. | |
| 5,536,656 A | 7/1996 | Kemp et al. | |
| 5,543,441 A | 8/1996 | Rhee et al. | |
| 5,565,210 A | 10/1996 | Rosenthal et al. | |
| 5,567,806 A | 10/1996 | Abdul-Malak et al. | |
| 5,569,273 A | 10/1996 | Titone et al. | |
| RE35,399 E | 12/1996 | Eisenberg | |
| 5,593,441 A | 1/1997 | Lichtenstein et al. | |
| 5,595,621 A | 1/1997 | Light et al. | |
| 5,601,571 A | 2/1997 | Moss | |
| 5,607,474 A | 3/1997 | Athanasiou et al. | |
| 5,607,590 A | 3/1997 | Shimizu | |
| 5,614,587 A | 3/1997 | Rhee et al. | |
| 5,618,551 A | 4/1997 | Tardy et al. | |
| 5,634,931 A | 6/1997 | Kugel | |
| 5,639,796 A | 6/1997 | Lee | |
| 5,665,391 A | 9/1997 | Lea | |
| 5,667,839 A | 9/1997 | Berg | |
| 5,681,568 A | 10/1997 | Goldin et al. | |
| 5,686,115 A | 11/1997 | Vournakis et al. | |
| 5,690,675 A | 11/1997 | Sawyer et al. | |
| 5,695,525 A * | 12/1997 | Mulhauser | A61F 2/0063 600/37 |
| 5,697,978 A | 12/1997 | Sgro | |
| 5,700,476 A | 12/1997 | Rosenthal et al. | |
| 5,700,477 A | 12/1997 | Rosenthal et al. | |
| 5,709,934 A | 1/1998 | Bell et al. | |
| 5,716,409 A | 2/1998 | Debbas | |
| 5,720,981 A | 2/1998 | Eisinger | |
| 5,732,572 A | 3/1998 | Litton | |
| 5,749,895 A | 5/1998 | Sawyer et al. | |
| 5,752,974 A | 5/1998 | Rhee et al. | |
| 5,766,246 A | 6/1998 | Mulhauser et al. | |
| 5,766,631 A | 6/1998 | Arnold | |
| 5,769,864 A | 6/1998 | Kugel | |
| 5,771,716 A | 6/1998 | Schlussel | |
| 5,785,983 A | 7/1998 | Furlan et al. | |
| 5,800,541 A | 9/1998 | Rhee et al. | |
| 5,814,328 A | 9/1998 | Gunasekaran | |
| 5,824,082 A | 10/1998 | Brown | |
| 5,833,705 A | 11/1998 | Ken et al. | |
| 5,840,011 A | 11/1998 | Landgrebe et al. | |
| 5,861,034 A | 1/1999 | Taira et al. | |

(56) References Cited

U.S. PATENT DOCUMENTS

| | | | |
|---|---|---|---|
| 5,863,984 A | 1/1999 | Doillon et al. | |
| 5,869,080 A | 2/1999 | McGregor et al. | |
| 5,871,767 A | 2/1999 | Dionne et al. | |
| 5,876,444 A | 3/1999 | Lai | |
| 5,891,558 A | 4/1999 | Bell et al. | |
| 5,899,909 A | 5/1999 | Claren et al. | |
| 5,906,937 A | 5/1999 | Sugiyama et al. | |
| 5,910,149 A | 6/1999 | Kuzmak | |
| 5,911,731 A | 6/1999 | Pham et al. | |
| 5,916,225 A | 6/1999 | Kugel | |
| 5,919,232 A | 7/1999 | Chaffringeon et al. | |
| 5,919,233 A | 7/1999 | Knopf et al. | |
| 5,922,026 A | 7/1999 | Chin | |
| 5,931,165 A | 8/1999 | Reich et al. | |
| 5,942,278 A | 8/1999 | Hagedorn et al. | |
| 5,962,136 A | 10/1999 | Dewez et al. | |
| 5,972,008 A * | 10/1999 | Kalinski | A61F 2/0095 206/440 |
| 5,972,022 A | 10/1999 | Huxel | |
| RE36,370 E | 11/1999 | Li | |
| 5,993,844 A | 11/1999 | Abraham et al. | |
| 5,994,325 A | 11/1999 | Roufa et al. | |
| 5,997,895 A | 12/1999 | Narotam et al. | |
| 6,001,895 A | 12/1999 | Harvey et al. | |
| 6,008,292 A | 12/1999 | Lee et al. | |
| 6,015,844 A | 1/2000 | Harvey et al. | |
| 6,039,686 A | 3/2000 | Kovac | |
| 6,042,534 A | 3/2000 | Gellman et al. | |
| 6,042,592 A | 3/2000 | Schmitt | |
| 6,043,089 A | 3/2000 | Sugiyama et al. | |
| 6,051,425 A | 4/2000 | Morota et al. | |
| 6,056,688 A | 5/2000 | Benderev et al. | |
| 6,056,970 A | 5/2000 | Greenawalt et al. | |
| 6,057,148 A | 5/2000 | Sugiyama et al. | |
| 6,063,396 A | 5/2000 | Kelleher | |
| 6,066,776 A | 5/2000 | Goodwin et al. | |
| 6,066,777 A | 5/2000 | Benchetrit | |
| 6,071,292 A | 6/2000 | Makower et al. | |
| 6,077,281 A | 6/2000 | Das | |
| 6,080,194 A | 6/2000 | Pachence et al. | |
| 6,083,522 A | 7/2000 | Chu et al. | |
| 6,120,539 A | 9/2000 | Eldridge et al. | |
| 6,132,765 A | 10/2000 | DiCosmo et al. | |
| 6,143,037 A | 11/2000 | Goldstein et al. | |
| 6,153,292 A | 11/2000 | Bell et al. | |
| 6,165,488 A | 12/2000 | Tardy et al. | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,179,872 B1 | 1/2001 | Bell et al. | |
| 6,197,325 B1 | 3/2001 | MacPhee et al. | |
| 6,197,934 B1 | 3/2001 | DeVore et al. | |
| 6,197,935 B1 | 3/2001 | Doillon et al. | |
| 6,210,439 B1 | 4/2001 | Firmin et al. | |
| 6,221,109 B1 | 4/2001 | Geistlich et al. | |
| 6,224,616 B1 | 5/2001 | Kugel | |
| 6,241,768 B1 | 6/2001 | Agarwal et al. | |
| 6,258,124 B1 | 7/2001 | Darois et al. | |
| 6,262,332 B1 | 7/2001 | Ketharanathan | |
| 6,264,702 B1 | 7/2001 | Ory et al. | |
| 6,267,772 B1 | 7/2001 | Mulhauser et al. | |
| 6,277,397 B1 | 8/2001 | Shimizu | |
| 6,280,453 B1 | 8/2001 | Kugel et al. | |
| 6,287,316 B1 | 9/2001 | Agarwal et al. | |
| 6,290,708 B1 | 9/2001 | Kugel et al. | |
| 6,306,424 B1 | 10/2001 | Vyakarnam et al. | |
| 6,312,474 B1 | 11/2001 | Francis et al. | |
| 6,328,686 B1 | 12/2001 | Kovac | |
| 6,334,872 B1 | 1/2002 | Termin et al. | |
| 6,383,201 B1 | 5/2002 | Dong | |
| 6,391,333 B1 | 5/2002 | Li et al. | |
| 6,391,939 B2 | 5/2002 | Tayot et al. | |
| 6,408,656 B1 | 6/2002 | Ory et al. | |
| 6,410,044 B1 | 6/2002 | Chudzik et al. | |
| 6,413,742 B1 | 7/2002 | Olsen et al. | |
| 6,428,978 B1 | 8/2002 | Olsen et al. | |
| 6,436,030 B2 | 8/2002 | Rehil | |
| 6,440,167 B2 | 8/2002 | Shimizu | |
| 6,443,964 B1 | 9/2002 | Ory et al. | |
| 6,447,551 B1 | 9/2002 | Goldmann | |
| 6,447,802 B2 | 9/2002 | Sessions et al. | |
| 6,448,378 B2 | 9/2002 | DeVore et al. | |
| 6,451,032 B1 | 9/2002 | Ory et al. | |
| 6,451,301 B1 | 9/2002 | Sessions et al. | |
| 6,454,787 B1 | 9/2002 | Maddalo et al. | |
| 6,477,865 B1 | 11/2002 | Matsumoto | |
| 6,479,072 B1 | 11/2002 | Morgan et al. | |
| 6,500,464 B2 | 12/2002 | Ceres et al. | |
| 6,509,031 B1 | 1/2003 | Miller et al. | |
| 6,511,958 B1 | 1/2003 | Atkinson et al. | |
| 6,514,286 B1 | 2/2003 | Leatherbury et al. | |
| 6,514,514 B1 | 2/2003 | Atkinson et al. | |
| 6,540,773 B2 | 4/2003 | Dong | |
| 6,541,023 B1 | 4/2003 | Andre et al. | |
| 6,548,077 B1 | 4/2003 | Gunasekaran | |
| 6,554,855 B1 | 4/2003 | Dong | |
| 6,559,119 B1 | 5/2003 | Burgess et al. | |
| 6,566,345 B2 | 5/2003 | Miller et al. | |
| 6,575,988 B2 | 6/2003 | Rousseau | |
| 6,576,019 B1 | 6/2003 | Atala | |
| 6,596,002 B2 | 7/2003 | Therin et al. | |
| 6,596,304 B1 | 7/2003 | Bayon et al. | |
| 6,599,323 B2 | 7/2003 | Melican et al. | |
| 6,599,524 B2 | 7/2003 | Li et al. | |
| 6,599,690 B1 | 7/2003 | Abraham et al. | |
| 6,613,348 B1 | 9/2003 | Jain | |
| 6,623,963 B1 | 9/2003 | Muller et al. | |
| 6,630,414 B1 | 10/2003 | Matsumoto | |
| 6,638,284 B1 | 10/2003 | Rousseau et al. | |
| 6,640,976 B1 * | 11/2003 | Franks-Farah | A61B 50/31 206/232 |
| 6,652,594 B2 | 11/2003 | Francis et al. | |
| 6,653,450 B1 | 11/2003 | Berg et al. | |
| 6,656,206 B2 | 12/2003 | Corcoran et al. | |
| 6,660,280 B1 | 12/2003 | Allard et al. | |
| 6,669,735 B1 | 12/2003 | Pelissier | |
| 6,682,760 B2 | 1/2004 | Noff et al. | |
| 6,685,714 B2 | 2/2004 | Rousseau | |
| 6,706,684 B1 | 3/2004 | Bayon et al. | |
| 6,706,690 B2 | 3/2004 | Reich et al. | |
| 6,719,795 B1 | 4/2004 | Cornwall et al. | |
| 6,723,335 B1 | 4/2004 | Moehlenbruck et al. | |
| D489,973 S * | 5/2004 | Root | D24/229 |
| 6,730,299 B1 | 5/2004 | Tayot et al. | |
| 6,736,823 B2 | 5/2004 | Darois et al. | |
| 6,743,435 B2 | 6/2004 | DeVore et al. | |
| 6,755,868 B2 | 6/2004 | Rousseau | |
| 6,769,546 B2 * | 8/2004 | Busch | A61B 17/3401 206/366 |
| 6,773,723 B1 | 8/2004 | Spiro et al. | |
| 6,783,554 B2 | 8/2004 | Amara et al. | |
| 6,790,213 B2 * | 9/2004 | Cherok | A61F 2/0063 602/44 |
| 6,790,454 B1 | 9/2004 | Abdul Malak et al. | |
| 6,793,078 B2 * | 9/2004 | Roshdy | B65D 1/36 206/366 |
| 6,800,082 B2 | 10/2004 | Rousseau | |
| 6,833,408 B2 | 12/2004 | Sehl et al. | |
| 6,835,336 B2 | 12/2004 | Watt | |
| 6,841,716 B1 * | 1/2005 | Tsutsumi | A61K 9/703 602/42 |
| 6,852,330 B2 | 2/2005 | Bowman et al. | |
| 6,869,938 B1 | 3/2005 | Schwartz et al. | |
| 6,893,653 B2 | 5/2005 | Abraham et al. | |
| 6,896,141 B2 * | 5/2005 | McMichael | A61B 50/30 206/370 |
| 6,896,904 B2 | 5/2005 | Spiro et al. | |
| 6,910,581 B2 * | 6/2005 | McMichael | A61B 50/30 206/370 |
| 6,911,003 B2 * | 6/2005 | Anderson | A61B 17/0401 600/30 |
| 6,936,276 B2 | 8/2005 | Spiro et al. | |
| 6,939,562 B2 | 9/2005 | Spiro et al. | |

(56) References Cited

U.S. PATENT DOCUMENTS

| | | |
|---|---|---|
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,976,584 B2 | 12/2005 | Maiola et al. |
| 6,977,231 B1 | 12/2005 | Matsuda |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,243,791 B2 | 7/2007 | Detruit et al. |
| 7,385,176 B2* | 6/2008 | Pfeiffer ............. A61B 5/14542 250/227.14 |
| 7,475,776 B2 | 1/2009 | Detruit et al. |
| 7,481,314 B2 | 1/2009 | Komarnycky |
| 7,594,921 B2 | 9/2009 | Browning |
| 7,615,065 B2 | 11/2009 | Priewe et al. |
| 7,670,380 B2 | 3/2010 | Cauthen, III |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,799,767 B2 | 9/2010 | Lamberti et al. |
| 7,806,905 B2 | 10/2010 | Ford et al. |
| 7,823,727 B2* | 11/2010 | Chappuis ............. G09F 3/0288 206/233 |
| 7,824,420 B2 | 11/2010 | Eldridge et al. |
| 7,828,854 B2* | 11/2010 | Rousseau ............. A61F 2/0063 606/151 |
| D631,558 S * | 1/2011 | Harmston .................... D24/229 |
| 8,033,395 B2 | 10/2011 | Iwao et al. |
| D650,912 S * | 12/2011 | Tomes ........................ D24/227 |
| 8,142,515 B2 | 3/2012 | Therin et al. |
| 8,197,837 B2 | 6/2012 | Jamiolkowski et al. |
| 8,226,669 B2* | 7/2012 | Detruit ................. A61F 2/0063 206/363 |
| 8,240,468 B2* | 8/2012 | Wilkinson ............. A61B 5/417 206/363 |
| 8,323,675 B2 | 12/2012 | Greenawalt |
| 8,366,787 B2 | 2/2013 | Brown et al. |
| 8,460,169 B2* | 6/2013 | Lund .................... A61F 2/0045 600/29 |
| 8,709,094 B2 | 4/2014 | Stad et al. |
| 8,846,060 B2 | 9/2014 | Archibald et al. |
| 8,877,233 B2 | 11/2014 | Obermiller et al. |
| 8,956,373 B2 | 2/2015 | Ford et al. |
| 9,034,357 B2 | 5/2015 | Stopek |
| 9,072,586 B2* | 7/2015 | Ranucci ............... A61F 2/0063 |
| 9,241,781 B2* | 1/2016 | Nentwick ........... A61B 17/0401 |
| 9,265,578 B2* | 2/2016 | Dacey .................. A61B 50/10 |
| D786,093 S * | 5/2017 | Christie .......................... D9/748 |
| 9,744,333 B2* | 8/2017 | Terzibashian ....... A61M 25/002 |
| 2002/0095218 A1 | 7/2002 | Carr et al. |
| 2002/0117408 A1 | 8/2002 | Solosko et al. |
| 2003/0086975 A1 | 5/2003 | Ringeisen |
| 2003/0114885 A1* | 6/2003 | Nova .................... A61N 1/046 607/2 |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0000499 A1 | 1/2004 | Maiola et al. |
| 2004/0034373 A1 | 2/2004 | Schuldt-Hempe et al. |
| 2004/0059356 A1 | 3/2004 | Gingras |
| 2004/0068159 A1 | 4/2004 | Neisz et al. |
| 2004/0101546 A1 | 5/2004 | Gorman et al. |
| 2004/0243214 A1* | 12/2004 | Farrell .................. A61F 2/0095 623/1.11 |
| 2005/0002893 A1 | 1/2005 | Goldmann |
| 2005/0021058 A1 | 1/2005 | Negro |
| 2005/0077197 A1 | 4/2005 | Detruit et al. |
| 2005/0085924 A1 | 4/2005 | Darois et al. |
| 2005/0098460 A1* | 5/2005 | Smith .................... A61B 50/30 206/366 |
| 2005/0113849 A1 | 5/2005 | Popadiuk et al. |
| 2005/0126948 A1 | 6/2005 | Maiola et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0192600 A1 | 9/2005 | Nicolo et al. |
| 2005/0232979 A1 | 10/2005 | Shoshan |
| 2005/0267521 A1 | 12/2005 | Forsberg |
| 2005/0277991 A1* | 12/2005 | Covey .................. A61N 1/0492 607/5 |
| 2005/0288691 A1 | 12/2005 | Leiboff |
| 2006/0135921 A1 | 6/2006 | Wiercinski et al. |
| 2006/0147501 A1 | 7/2006 | Hillas et al. |
| 2006/0196788 A1* | 9/2006 | Komarnycky ........ A61F 2/0045 206/287 |
| 2006/0216320 A1 | 9/2006 | Kitazono et al. |
| 2006/0252981 A1 | 11/2006 | Matsuda et al. |
| 2007/0209957 A1 | 9/2007 | Glenn et al. |
| 2007/0299538 A1 | 12/2007 | Roeber |
| 2008/0027291 A1* | 1/2008 | Williams-Hartman ...................... A61J 7/0481 600/300 |
| 2008/0286144 A1* | 11/2008 | Shalaby .................... A61L 2/08 422/22 |
| 2009/0099579 A1* | 4/2009 | Nentwick .......... A61B 17/0401 606/151 |
| 2009/0166236 A1 | 7/2009 | Iwao et al. |
| 2009/0209031 A1 | 8/2009 | Stopek |
| 2009/0228021 A1* | 9/2009 | Leung ............. A61B 17/06166 606/139 |
| 2010/0158991 A1 | 6/2010 | Okada et al. |
| 2010/0286715 A1 | 11/2010 | Detruit et al. |
| 2010/0288770 A1 | 11/2010 | Marco et al. |
| 2010/0307941 A1* | 12/2010 | Tomes ................... A61M 25/00 206/366 |
| 2010/0311026 A1* | 12/2010 | Tomes ................ A61M 25/002 434/262 |
| 2011/0082479 A1* | 4/2011 | Friedlander ........... A61F 2/0063 606/151 |
| 2011/0232234 A1* | 9/2011 | Lockwood ............ A61M 25/00 53/443 |
| 2011/0284410 A1* | 11/2011 | Lockwood ............... B65D 1/36 206/364 |
| 2011/0309073 A1* | 12/2011 | Dacey .................. A61F 2/0095 220/6 |
| 2012/0059388 A1* | 3/2012 | Knowles ................ A61B 17/29 606/108 |
| 2012/0210678 A1* | 8/2012 | Alcouloumre ... A61B 17/06114 53/467 |
| 2013/0035704 A1* | 2/2013 | Dudai ................... A61F 2/0063 606/151 |
| 2014/0090999 A1* | 4/2014 | Kirsch ............... A61B 17/0057 206/438 |
| 2015/0176303 A1 | 6/2015 | Kuchar ................... B65D 65/38 428/136 |
| 2015/0268215 A1* | 9/2015 | Tomellini ............. G01N 33/227 436/93 |
| 2016/0228676 A1* | 8/2016 | Glithero ............. A61M 25/002 |
| 2016/0310253 A1* | 10/2016 | Ferrand ..................... B65B 7/02 |
| 2016/0310254 A1* | 10/2016 | Ferrand ................... B65D 11/14 |

(56) References Cited

U.S. PATENT DOCUMENTS

| | | | |
|---|---|---|---|
| 2017/0131258 A1* | 5/2017 | Tomellini | G01N 33/227 |
| 2017/0216558 A1* | 8/2017 | Hughett | A61M 25/002 |

FOREIGN PATENT DOCUMENTS

| | | |
|---|---|---|
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 544485 A1 | 6/1993 |
| EP | 0552576 A1 | 7/1993 |
| EP | 614650 A2 | 9/1994 |
| EP | 0621014 A1 | 10/1994 |
| EP | 0 625 334 A1 | 11/1994 |
| EP | 0625334 A1 | 11/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 827724 A2 | 3/1998 |
| EP | 0836838 A1 | 4/1998 |
| EP | 0895762 A2 | 2/1999 |
| EP | 898944 A2 | 3/1999 |
| EP | 1017415 A1 | 7/2000 |
| EP | 1052319 A1 | 11/2000 |
| EP | 1055757 A1 | 11/2000 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2715405 A1 | 7/1995 |
| FR | 2 724 563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 A1 | 3/2005 |
| FR | 2863277 A1 | 6/2005 |
| FR | 2884706 A1 | 10/2006 |
| GB | 2 051 153 A | 1/1981 |
| JP | H0332677 A | 2/1991 |
| JP | H05237128 A | 9/1993 |
| JP | H09137380 A | 5/1997 |
| TM | 93/11805 A1 | 6/1993 |
| WF | 98/35632 A1 | 8/1998 |
| WO | 89/02445 A1 | 3/1989 |
| WO | 89/08467 A1 | 9/1989 |
| WO | 90/12551 A1 | 11/1990 |
| WO | 92/06639 A2 | 4/1992 |
| WO | 92/20349 A1 | 11/1992 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 02/007648 A1 | 1/2002 |
| WO | 02/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 200511280 A1 | 2/2005 |
| WO | 2005013863 A2 | 2/2005 |
| WO | 2005018698 A1 | 3/2005 |
| WO | 2005105172 A1 | 11/2005 |
| WO | 2006018552 A1 | 2/2006 |
| WO | 2006023444 A2 | 3/2006 |
| WO | WO 2006/100372 A1 | 9/2006 |
| WO | 2007048099 A2 | 4/2007 |
| WO | 2009031035 A2 | 3/2009 |
| WO | 2009071998 A2 | 6/2009 |
| WO | 2011128903 A2 | 10/2011 |
| WO | WO 2011/128903 A2 | 10/2011 |

OTHER PUBLICATIONS

Ellouali, M. et al., "Antitumor Activity of Low Molecular Weight Fucans Extracted from Brown Seaweed Ascophyllum Nodosum," Anticancer Res., Nov.-Dec. 1993, pp. 2011-2020, 12 (6A).

Malette, W. G. et al., "Chitosan, A New Hemostatic," Ann Th. Surg., Jul. 1983, pp. 55-58, 36.

Langenbech, M. R. et al., "Comparison of biomaterials in the early postoperative period," Surg Endosc., May 2003, pp. 1105-1109, 17 (7).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.

Junge, K. et al., "Functional and Morphologic Properties of a Modified Mesh for Inguinal Hernia Repair," World J. Surg., Sep. 2002, pp. 1472-1480, 26.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Welty, G. et al., "Functional impairment and complaints following incisional hernia repair with different polypropylene meshes," Hernia, Aug. 2001; pp. 142-147, 5.

Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug., pp. 2285-2292, 22(4).

Scheidbach, H. et al., "In vivo studies comparing the biocompatibility of various polypropylene meshes and their candling properties during endoscopic total extraperitoneal (TEP) patchplasty: An experimental study in pigs," Surg. Endosc., Feb. 2004, pp. 211-220,18(2).

(56) References Cited

OTHER PUBLICATIONS

Blondin, C. et al., "Inhibition of Complement Activation by Natural Sulfated Polysaccharides (Fucans) from Brown Seaweed," Molecular Immuol., Mar. 1994, pp. 247-253, 31(4).

Zvyagintseva, T. et al., "Inhibition of complement activation by water-soluble polysaccharides of some far-eastern brown seaweeds," Comparative Biochem and Physiol, Jul. 2000, pp. 209-215,126(3).

Rosen, M. et al., "Laparoscopic component separation in the single-stage treatment of infected abdominal wall prosthetic removal," Hernia, 2007, pp. 435-440, 11, published online Jul. 2007.

Amid, P., "Lichtenstein tension-free hernioplasty: Its inception, evolution, and principles," Hernia, 2004; pp. 1-7, 8, published online Sep. 2003.

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Muzzarelli, R. et al., "Reconstruction of parodontal tissue with chitosan," Biomaterials, Nov. 1989, pp. 598-604, 10.

Haroun-Bouhedja, F. et al., "Relationship between sulfate groups and biological activities of fucans," Thrombosis Res., Dec. 2000, pp. 453-459, 100(5).

Blondin, C. et al., "Relationships between chemical characteristics and anticomplementary activity of fucans," Biomaterials, Mar. 1996, pp. 597-603, 17(6).

Strand, S. et al., "Screening of Chitosans and Conditions for Bacterial Flocculation," Biomacromolecules, Mar. 2001, 126-133, 2.

Kanabar, V. et al., "Some structural determinants of the antiproliferative effect of heparin-like molecules on human airway smooth muscle," Br. J. Pharmacol., Oct. 2005, pp. 370-777, 146(3).

Hirano, S. et al., "The blood biocompatibility of chitosan and N-acylchitosans," J. Biomed. Mater. Res., Apr. 1985, 413-417, 19.

Rao, B. et al., "Use of chitosan as a biomaterial: Studies on its safety and hemostatic potential," J. Biomed. Mater. Res., Jan. 1997, pp. 21-28, 34.

Prokop, A. et al., "Water Soluble Polymers for Immunoisolation I: Complex Coacevation and Cytotoxicity," Advances in Polymer Science, Jul. 1998, pp. 1-51, 136.

Collins, R. et al., "Use of collagen film as a dural substitute: Preliminary animal studies," Journal of Biomedical Materials Research, Feb. 1991, pp. 267-276, vol. 25.

Preliminary Search Report from French Patent Office dated Dec. 20, 2006, 3 pages.

European Office Action dated Apr. 1, 2016 in corresponding European Patent Application No. 13824648.3, 6 pages.

International Search Report for PCT/IB2013/002844 date of completion is May 16, 2014 (3 pages).

\* cited by examiner

PACKAGING FOR A HERNIA REPAIR DEVICE

CROSS-REFERENCE TO RELATED APPLICATIONS

This application is a National Stage Application of PCT/IB2013/002844 under 35USC § 371 (a), which claims priority of U.S. Provisional Patent Application Ser. No. 61/706,912 filed Sep. 28, 2012, the disclosures of each of the above-identified applications are hereby incorporated by reference in their entirety.

BACKGROUND

Technical Field

The present disclosure relates to packaging of surgical devices and, more particularly, to packaging for a hernia repair device.

Background of Related Art

Wound closure devices such as sutures, filaments, and staples, as well as other repair devices, such as mesh or patch reinforcements, are frequently used to repair tissue defects, e.g., herniated tissue, and other damaged and/or diseased tissue. For example, in the case of hernias, a surgical mesh or patch is commonly used to reinforce the abdominal wall. The surgical mesh is typically held in place by adhering, suturing, or stapling the surgical mesh to the tissue surrounding the defect.

Some surgical meshes have been developed which incorporate pre-determined fold lines, sutures, and/or other features to facilitate the insertion, positioning, and/or attachment of the surgical mesh to the abdominal wall. However, such meshes may become tangled, disorientated, and/or damaged, e.g., during transport, storage, or removal from packaging. Accordingly, it would be desirable to provide packaging for a surgical mesh that inhibits tangling or damage to the surgical mesh and maintains proper orientation of the surgical mesh, thereby facilitating removal of the surgical mesh from the packaging and subsequent use thereof.

SUMMARY

A first aspect of the invention is a packaging member for a hernia repair device including a surgical mesh and at least one grasping member, the packaging member comprising:
  a central portion configured to receive the surgical mesh;
  at least one recessed track section configured to receive the at least one grasping member; and
  a knob extending into the at least one recessed track section, the knob configured to retain the at least one grasping member within the at least one recessed track section.

In embodiments, the hernia repair device defines a folding axis, the packaging member further including a pair of indicia indicating a location of the folding axis. In embodiments, the central portion includes a recess configured to receive the surgical mesh. In embodiments, the packaging member further comprises at least one finger-receiving portion positioned adjacent the at least one recessed track section, the at least one finger-receiving portion configured to facilitate grasping of the at least one grasping member for removal from the packaging member. In embodiments, the packaging member further comprises a protective film configured for positioning about the packaging member to maintain the hernia repair device in a sterile state. In embodiments, the packaging member further includes a tab configured to facilitate separation of the protective film from the packaging member. In embodiments, the packaging member further comprises grasping indicia disposed on the central portion, the grasping indicia positioned to indicate grasping positions for grasping the surgical mesh. In embodiments wherein the hernia repair device includes a pair of opposed grasping members, the packaging member further comprises a pair of opposed recessed track sections configured to receive the opposed grasping members. In embodiments wherein the hernia device includes first and second grasping members coupled to the surgical mesh; the packaging member further comprises first and second opposed recessed track sections disposed about the central portion, the first and second opposed recessed track sections configured to receive the first and second grasping members, respectively. In embodiments, the packaging member further includes first and second knobs extending into the first and second track sections, the first and second knobs configured to retain the first and second grasping members within the first and second track sections, respectively. In embodiments, the packaging member further includes at least one finger-receiving portion positioned adjacent the first and second track sections, the at least one finger-receiving portion configured to facilitate grasping of the first and second grasping members for removal from the packaging member.

A second aspect of the invention is a surgical package comprising a packaging member as described above and a hernia repair device including a surgical mesh and at least one grasping member. In embodiments, the surgical mesh having first and second support members defining a folding axis therebetween; and first and second grasping members coupled to the surgical mesh, the first grasping member is disposed on a first side of the folding axis and the second grasping member is disposed on a second side of the folding axis, the central portion including at least one indicia configured to indicate a location of the folding axis.

In accordance with embodiments of the present disclosure, a packaging member is provided for a hernia repair device including a surgical mesh and one or more grasping members. The packaging member includes a central portion configured to receive the surgical mesh, one or more recessed track sections configured to receive the one or more grasping members, and a knob extending into the one or more recessed track sections. The knob is configured to retain the grasping member(s) within the recessed track section(s).

In embodiments, the hernia repair device defines a folding axis and the packaging member further including indicia indicating a location of the folding axis.

In embodiments, the central portion of the packaging member includes a recess configured to receive the surgical mesh.

In embodiments, the packaging member further includes one or more finger-receiving portions positioned adjacent the recessed track section(s).

In embodiments, the packaging member further includes a protective film configured for positioning about the packaging member to maintain the hernia repair device in a sterile state. Further, the packaging member may include a tab configured to facilitate separation of the protective film from the packaging member.

In embodiments, the packaging member further includes grasping indicia disposed on the central portion. The grasping indicia are positioned to indicate grasping positions for grasping the surgical mesh.

In embodiments, the hernia repair device includes a pair of opposed grasping members. In such an embodiment, the packaging member includes a pair of opposed recessed track sections configured to receive the opposed grasping members.

In accordance with embodiments of the present disclosure, a surgical package is provided including a hernia repair device and a packaging member. The hernia repair device includes a surgical mesh and first and second grasping members coupled to the surgical mesh. The packaging member is configured for retaining the hernia repair device and includes a central portion configured to receive the surgical mesh and first and second opposed recessed track sections disposed about the central portion. The first and second opposed recessed track sections are configured to receive the first and second grasping members, respectively. The surgical package may otherwise be configured similarly to any or all of the embodiments above.

In accordance with embodiments of the present disclosure, a surgical package is provided. The surgical package includes a hernia repair device and a packaging member for retaining the hernia repair device. The hernia repair device includes a surgical mesh having first and second support members defining a folding axis therebetween and first and second grasping members coupled to the surgical mesh. The first grasping member is disposed on a first side of the folding axis and the second grasping member is disposed on a second side of the folding axis. The packaging member includes a central portion and first and second opposed recessed track sections. The central portion is configured to receive the surgical mesh and includes one or more indicia configured to indicate a location of the folding axis. The first and second opposed recessed track sections are disposed about the central portion and are configured to receive the first and second grasping members, respectively. The surgical package may otherwise be configured similarly to any or all of the embodiments above.

The present disclosure further relates to a packaging member and to surgical devices as defined in the following clauses:

Clause 1. A packaging member for a hernia repair device including a surgical mesh and at least one grasping member, the packaging member comprising:
  a central portion configured to receive the surgical mesh;
  at least one recessed track section configured to receive the at least one grasping member; and
  a knob extending into the at least one recessed track section, the knob configured to retain the at least one grasping member within the at least one recessed track section.

Clause 2. The packaging member according to clause 1, wherein the hernia repair device defines a folding axis, the packaging member further including a pair of indicia indicating a location of the folding axis.

Clause 3. The packaging member according to clause 1, wherein the central portion includes a recess configured to receive the surgical mesh.

Clause 4. The packaging member according to clause 1, further comprising at least one finger-receiving portion positioned adjacent the at least one recessed track section, the at least one finger-receiving portion configured to facilitate grasping of the at least one grasping member for removal from the packaging member.

Clause 5. The packaging member according to clause 1, further comprising a protective film configured for positioning about the packaging member to maintain the hernia repair device in a sterile state.

Clause 6. The packaging member according to clause 5, wherein the packaging member further includes a tab configured to facilitate separation of the protective film from the packaging member.

Clause 7. The packaging member according to clause 1, further comprising grasping indicia disposed on the central portion, the grasping indicia positioned to indicate grasping positions for grasping the surgical mesh.

Clause 8. The packaging member according to clause 1, wherein the hernia repair device includes a pair of opposed grasping members and wherein the packaging member further comprises a pair of opposed recessed track sections configured to receive the opposed grasping members.

Clause 9. A surgical package, comprising:
  a hernia repair device, including:
    a surgical mesh; and
    first and second grasping members coupled to the surgical mesh; and
  a packaging member for retaining the hernia repair device, the package member including:
    a central portion configured to receive the surgical mesh; and
      first and second opposed recessed track sections disposed about the central portion, the first and second opposed recessed track sections configured to receive the first and second grasping members, respectively.

Clause 10. The surgical package according to clause 9, wherein the packaging member further includes first and second knobs extending into the first and second track sections, the first and second knobs configured to retain the first and second grasping members within the first and second track sections, respectively.

Clause 11. The surgical package according to clause 9, further comprising a protective film configured for positioning about the packaging member to maintain the hernia repair device in a sterile state.

Clause 12. The surgical package according to clause 9, wherein the hernia repair device defines a folding axis and wherein the packaging member includes a pair of indicia indicating a location of the folding axis.

Clause 13. The surgical package according to clause 9, further comprising grasping indicia disposed on the central portion of the packaging member, the grasping indicia positioned to indicate grasping positions for grasping the surgical mesh.

Clause 14. A surgical package, comprising:
  a hernia repair device, including:
    a surgical mesh having first and second support members defining a folding axis therebetween; and
    first and second grasping members coupled to the surgical mesh, the first grasping member disposed on a first side of the folding axis and the second grasping member disposed on a second side of the folding axis; and
  a packaging member for retaining the hernia repair device, the package member including:
    a central portion configured to receive the surgical mesh, the central portion including at least one indicia configured to indicate a location of the folding axis; and
    first and second opposed recessed track sections disposed about the central portion, the first and second opposed recessed track sections configured to receive the first and second grasping members, respectively.

Clause 15. The surgical package according to clause 14, wherein the packaging member further includes first and second knobs extending into the first and second track sections, the first and second knobs configured to retain the first and second grasping members with the first and second track sections, respectively.

Clause 16. The surgical package according to clause 14, wherein the central portion of the packaging member includes a recess configured to receive the surgical mesh.

Clause 17. The surgical package according to clause 14, wherein the packaging member further includes at least one finger-receiving portion positioned adjacent the first and second track sections, the at least one finger-receiving portion configured to facilitate grasping of the first and second grasping members for removal from the packaging member.

Clause 18. The surgical package according to clause 14, further comprising a protective film configured for positioning about the packaging member to maintain the hernia repair device in a sterile state.

Clause 19. The surgical package according to clause 18, wherein the packaging member further includes a tab configured to facilitate separation of the protective film from the packaging member.

Clause 20. The surgical package according to clause 14, further comprising grasping indicia disposed on the central portion of the packaging member, the grasping indicia positioned to indicate grasping positions for grasping the surgical mesh.

BRIEF DESCRIPTION OF THE DRAWINGS

Various embodiments of the present disclosure are described herein with reference to the drawings wherein.

DETAILED DESCRIPTION

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 1:
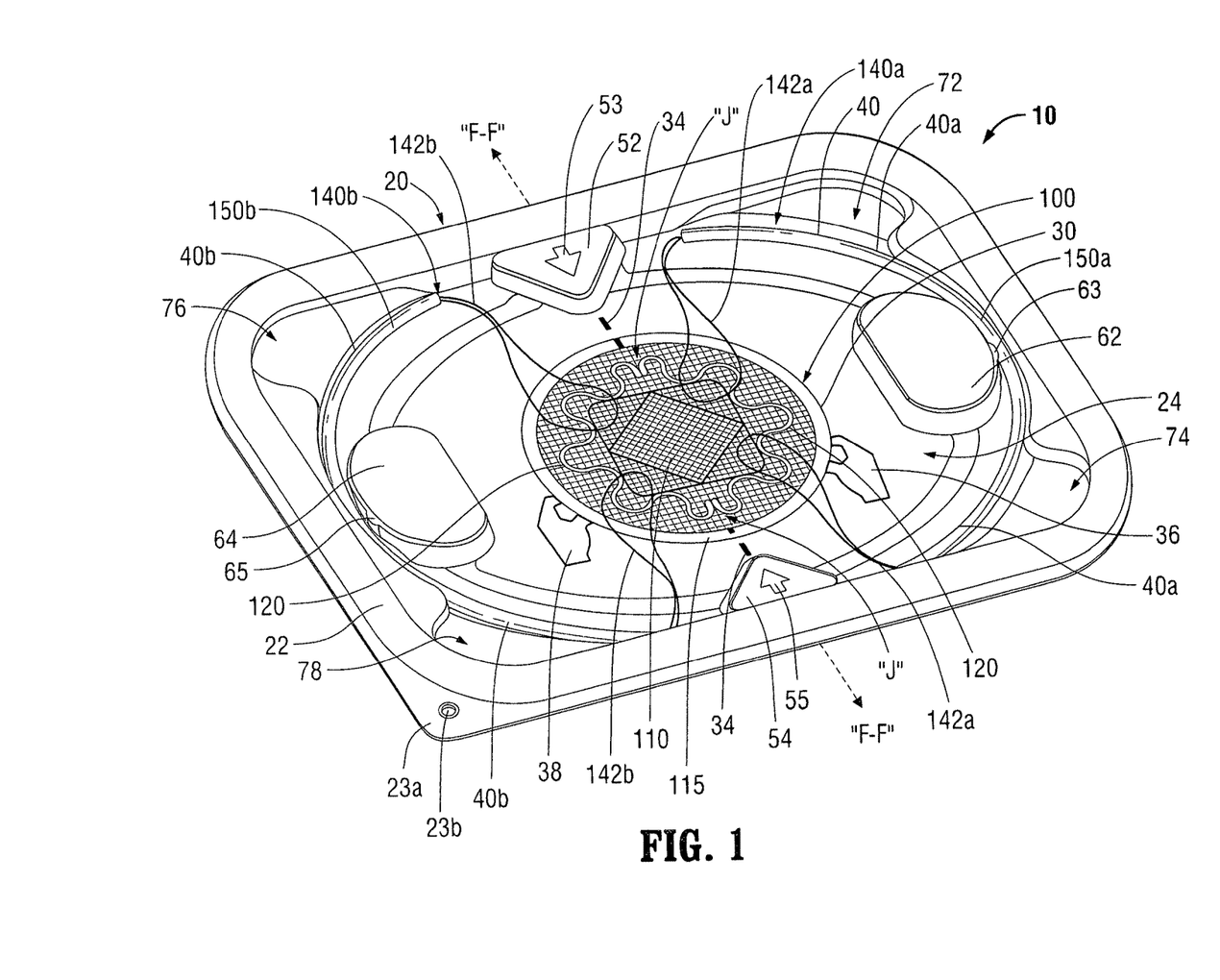
FIG. 1 is a top, perspective view of a packaging member for a hernia repair device provided in accordance with the present disclosure, shown retaining a hernia repair device therein.

Turning now to FIG. 1, a packaging member (generally designated by reference numeral 10) provided in accordance with the present disclosure is configured for retaining a hernia repair device 100. Although packaging member 10 is shown and described herein as being configured for use with hernia repair device 100, it is envisioned that packaging member 10 may be configured for use with any suitable hernia repair device so as to facilitate the removal of the hernia repair device from packaging member 10 while maintaining proper orientation of the device and inhibiting tangling or damaging the device. That is, although different hernia repair devices may necessitate various different configurations of packaging member 10, the features of packaging member 10 remain generally consistent regardless of the particular hernia repair device used. For the purposes herein, hernia repair device 100 is generally described.

Figure 2:
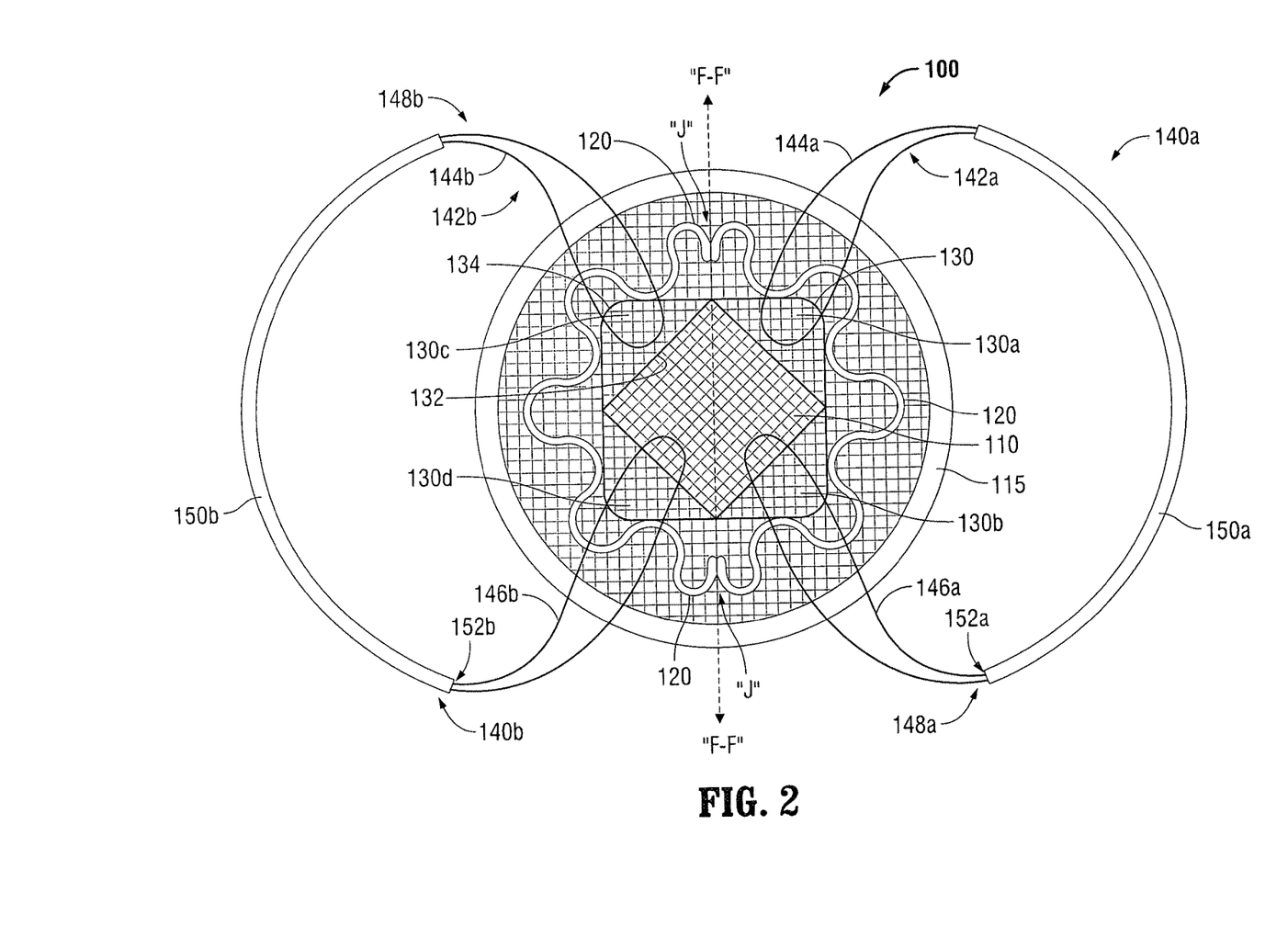
FIG. 2 is a top, perspective view of the hernia repair device of FIG. 1.

Referring to FIG. 2, hernia repair device 100 generally includes a surgical mesh 110 having a support member 120 coupled thereto, a plurality of flaps 130, and a pair of grasping members 140a, 140b. Surgical mesh 110 is configured for insertion into a tissue defect and is dimensioned to extend across the tissue defect. Surgical mesh 110 may be formed from one or more types of monofilament or multi-filament fibers from a biocompatible material such as, for example, polypropylene, polyethylene terephthalate (PET), or any other suitable synthetic or natural material. Surgical mesh 110 further include a film 115 disposed, using techniques within the purview of those skilled in the art, on the distal surface thereof to inhibit adhesion of organ tissue to the distal surface of surgical mesh 110. Any material that inhibits adhesion can be used to make film 115 such as, for example, collagen-based compositions or polytetrafluoroethylene (PTFE).

Support member 120 defines a generally annular shape and may be formed from any suitable material, e.g., an absorbable or non-absorbable biocompatible polymer. Support member 120 is secured to surgical mesh 110 towards an outer periphery of surgical mesh 110, e.g., annularly about surgical mesh 110, and is configured to provide structural support to surgical mesh 110, while also facilitating the insertion of surgical mesh 110 into, and the positioning of surgical mesh 110 within, the tissue defect. In particular, support member 120 is overmolded onto surgical mesh 110 to secure flaps 130 to mesh 110. Junctions "J" of support member 120 cooperate to define a folding axis "F-F" that allows surgical mesh 110 to be folded about folding axis "F-F" to facilitate insertion of surgical mesh 110 into a tissue defect.

Continuing with reference to FIG. 2, as mentioned above, hernia repair device 100 further includes a plurality of flaps 130 coupled to surgical mesh 110, e.g., four (4) flaps 130a, 130b, 130c, 130d (collectively referred to as flaps 130). Flaps 130 may be made from the same materials described above in connection with surgical mesh 110 and may be made from the same or different material as surgical mesh 110. Each flap 130 extends from a fixed end 132 that is engaged to surgical mesh 110, e.g., via the overmolding of support member 120 onto fixed ends 132 of flaps 130 and surgical mesh 110 to a free end 134. Flaps 130 extend proximally from mesh 110 to facilitate attachment of flaps 130 to tissue.

Grasping members 140a, 140b each include a loop of filament 142a, 142b and an overtube 150a, 150b, respectively. Filaments 142a, 142b may be made from suture, threading, wire, or any other suitable biocompatible material. The material forming filaments 142a, 142b is not critical in that, as will be described below, filaments 142a, 142b are removed from hernia repair device 100 after implantation and discarded. Each filament loop 142a, 142b includes a first end 144a, 144b, a second end 146a, 146b, and an intermediate segment 148a, 148b. The first end 144a, 144b of each filament loop 142a, 142b is disposed through one of the flaps 130. The second end 146a, 146b of each filament loop 142a, 142b is coupled, e.g., disposed through, an adjacent flap 130. More specifically, as shown in FIG. 2, first end 144a of filament loop 142a is coupled to flap 130a, while second end 146a of filament loop 142a is coupled to flap 130b. Similarly, first end 144b of filament loop 142b is coupled to flap 130c, while second end 146b of filament loop 142b is coupled to flap 130d.

Each grasping member 140a, 140b further includes an overtube 150a, 150b disposed about at least a portion of intermediate segment 148a, 148b of the respective filament loop 142a, 142b. Overtubes 150a, 150b of grasping members 140a, 140b, respectively, each defines a lumen 152a, 152b extending longitudinally therethrough to permit passage of respective filament loops 142a, 142b therethrough. Overtubes 150a, 150b provide an ergonomic grasping surface to facilitate grasping of filament loops 142a, 142b by the clinician, e.g., to approximate surgical mesh 110 relative to tissue and/or to manipulate flaps 130.

Figure 4:
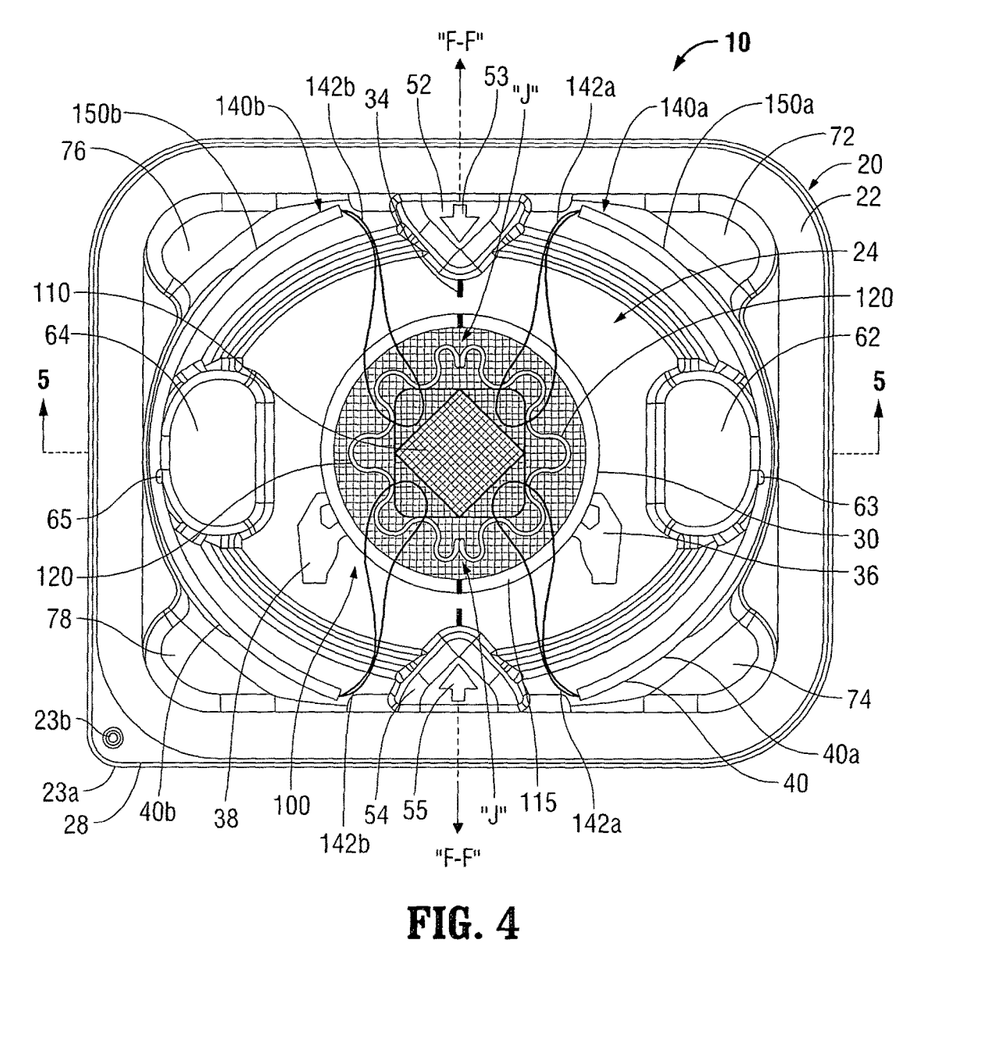
FIG. 4 is a plan view of the packaging member of FIG. 1 including the hernia repair device of FIG. 2 engaged therein.
Figure 5:
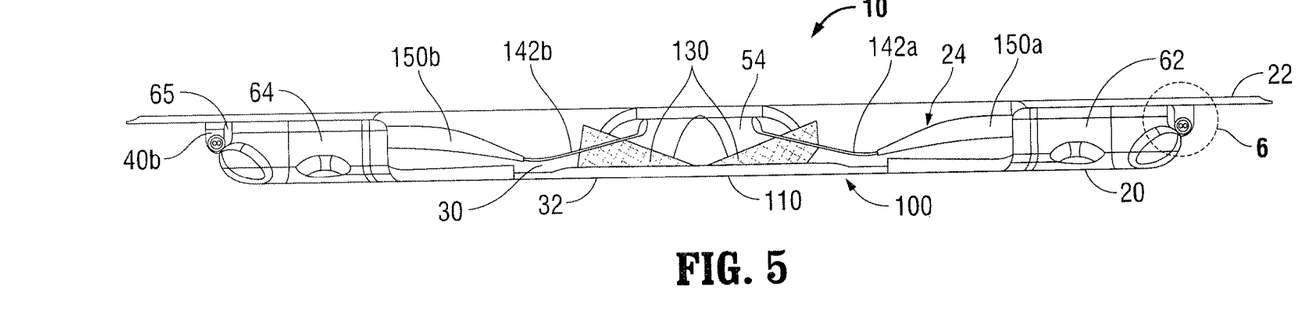
FIG. 5 is a cross-sectional view of the packaging member of FIG. 1 taken across section line 5-5 of FIG. 4.
Figure 6:
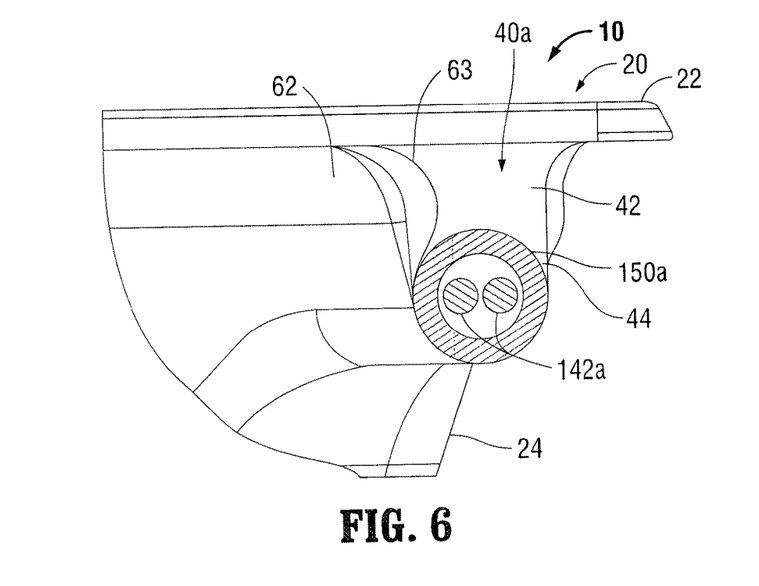
FIG. 6 is an enlarged view of the area of detail indicated as "6" in FIG. 5.

Turning now to FIGS. 4-6, packaging member 10, as mentioned above, is configured to retain hernia repair device 100 therein so as to inhibit tangling or damage to hernia repair device 100 and to maintain proper orientation of hernia repair device 100. Packaging member 10 generally includes a base 20 having a peripheral flange 22 surrounding a recessed portion 24 that is configured to receive hernia repair device 100. Base 20 may be formed from any suitable polymer or other material, e.g., paperboard or fiberboard (either of which may be coated with a polymer or foil or may be uncoated), via molding, e.g., vacuum molding or injection molding, or other suitable process. A protective film 28 covering recessed portion 24 of base 20 and sealed to peripheral flange 22, e.g., via heat sealing or adhesion, may be provided to maintain hernia repair device 100 in a sterile state. Film 28 may be formed from any suitable material such as, for example, Tyvek®, which allows hernia repair device 100 to be sterilized once sealed within packaging member 10. Peripheral flange 22 is provided with a tab member 23a including a projection 23b extending therefrom to facilitate grasping of protective film 28, separation of protective film 28 from peripheral flange 22, and removal of protective film 28 from base 20 in preparation for use.

Where moisture-sensitive materials are incorporated into hernia repair device 100, the entire packaging member 10 can be placed within a moisture-impervious envelope (not shown). The moisture-impervious envelope (not shown) can be made from, for example, a foil laminate using techniques known to those skilled in the art.

With continued reference to FIGS. 4-6, recessed portion 24 of base 20 of packaging member 10 generally includes a central recess 30 configured to receive surgical mesh 110 of hernia repair device 100, a recessed annular track 40 disposed annularly about central recess 30 and configured to receive grasping members 140a, 140b of hernia repair device 100, a pair of opposed indicator protrusions 52, 54 interrupting annular track 40 at opposed locations, and a pair of engagement protrusions 62, 64 that are opposed relative to one another and disposed in generally perpendicular orientation relative to indicator protrusions 52, 54. Recessed portion 24 further includes a first pair of finger-receiving portions 72, 74 disposed adjacent annular track 40 on either side of engagement protrusion 62 to facilitate disengagement and removal of gripping member 140a from annular track 40 and a second pair of finger-receiving portions 76, 78 disposed adjacent annular track 40 on either side of engagement protrusion 64 to facilitate disengagement of gripping member 140b from annular track 40.

As mentioned above, central recess 30 of recessed portion 24 of base 20 of packaging member 10 is configured to receive surgical mesh 110 of hernia repair device 100. Central recess 30 may include a further recessed floor 32 (see FIG. 5) configured to receive surgical mesh 110. Alternatively, central recess 30 may be configured to receive surgical mesh 110 on the surface thereof, or may include a raised platform (not shown) configured to receive surgical mesh 110. In either of these configurations, surgical mesh 110 is positioned within central recess 30 with flaps 130 facing upward, i.e., with film 115 disposed adjacent the surface of central recess 30, and such that the folding axis "F-F" of surgical mesh 110, as defined by the junctions "J" of support member 120, is aligned with arrows 53, 55 of indicator protrusions 52, 54 and indicator line 34, which extends along the floor of central recess 30 between indicator protrusions 52, 54. As such, the orientation of hernia repair device 100 when disposed within packaging member 10 can be readily ascertained.

Figure 3:
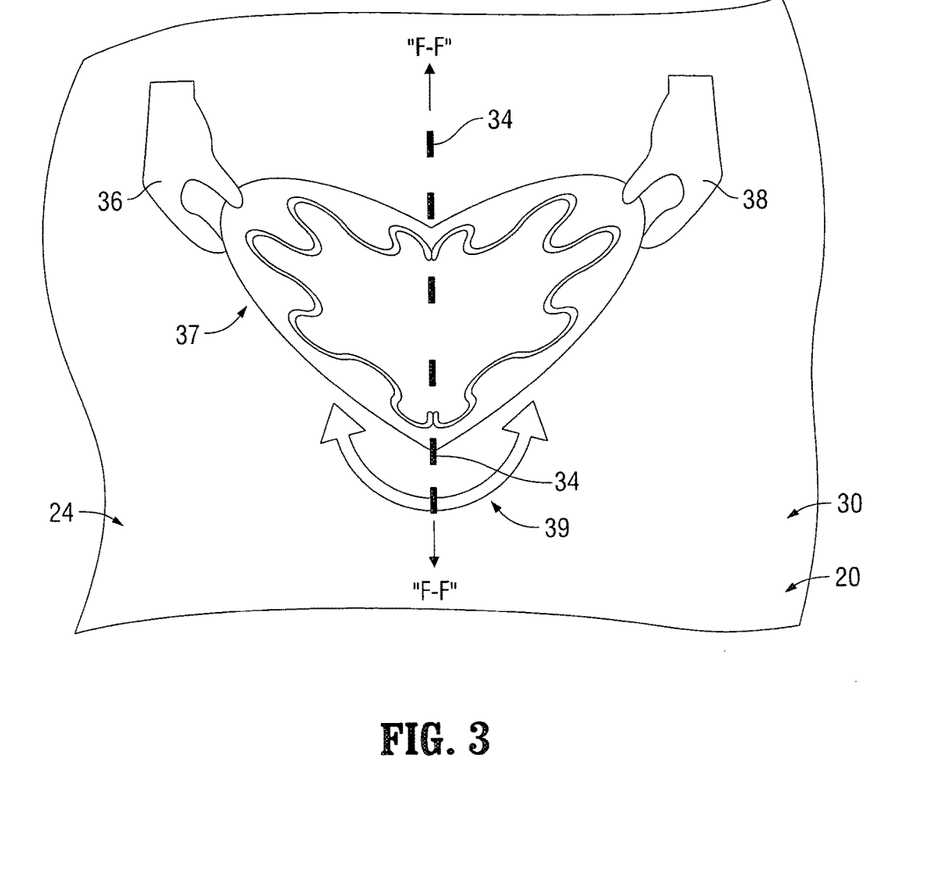
FIG. 3 is an enlarged view of a central portion of the packaging member of FIG. 1 showing the indicia provided thereon.

With additional reference to FIG. 3, central recess 30 further includes indicia 36-39 disposed on the floor of central recess 30. Indicia 36, 38 include illustrations of a user's left and right hands, respectively, positioned to indicate to the clinician where to grasp surgical mesh 110. Indicium 37 illustrates the surgical mesh during folding. Indicium 39 illustrates an arrow indicating the direction of folding. As can be appreciated, indicia 36-39, in conjunction with indicator line 34 and arrows 53, 55, provide guidance to the clinician to facilitate grasping of hernia repair device 100, removal of hernia repair device 100 from base 20, and folding of hernia repair device 100 along folding axis "F-F" in preparation for insertion into a tissue defect.

Continuing with reference to FIGS. 4-6, as mentioned, above, recessed annular track 40 is configured to receive grasping members 140a, 140b of hernia repair device 100 and is interrupted by opposed indicator protrusions 52, 54. More specifically, opposed indicator protrusions 52, 54 separate recessed annular track 40 into first and second semi-annular recessed track sections 40a, 40b, respectively. Track sections 40a, 40b generally oppose one another and are configured to receive grasping members 140a, 140b, respectively, of hernia repair device 100. Accordingly, recessed track sections 40a, 40b define width dimensions that are similar to or slightly larger than the diameter of overtubes 150a, 150b of grasping member 140a, 140b of hernia repair device 100 so as to be capable of receiving overtubes 150a, 150b without requiring deformation, or requiring minimal deformation, of overtubes 150a, 150b of hernia repair device 100 and/or base 20 of packaging member 10.

Engagement protrusions 62, 64 extend along and define, e.g., share a common wall, with at least a portion of track sections 40a, 40b, respectively. Each engagement protrusion 62, 64 further include a knob 63, 65 that extends into respective track sections 40a, 40b so as to decrease the width dimension of track sections 40a, 40b over at least a portion thereof. More specifically, as best shown in FIG. 6, knob 63 of engagement protrusion 62 extends into an upper portion 42 of track section 40a such that the upper portion 42 of track section 40a adjacent knob 63 defines a reduced width dimension that is smaller than the diameter of overtube 150a. As a result of this configuration, overtube 150a is required to be deformed and/or base 20 of packaging member 10 to be flexed to permit insertion of overtube 150a into lower portion 44 of track section 40a, e.g., to pass beyond knob 63. Once positioned within lower portion 44 of track section 40a, overtube 150a is resiliently returned to its at-rest dimensions and/or base 20 is returned to its un-flexed position, such that knob 63 inhibits overtube 150a from being withdrawn from track section 40a in the absence of sufficient urging to permit passage of overtube 150a beyond knob 63. Knob 65 of engagement protrusion 64 functions similarly with respect to track section 40b and overtube 150b.

Referring still to FIGS. 4-6, first and second pairs of finger-receiving portions 72, 74 and 76, 78, respectively, as mentioned above, are disposed adjacent first and second track sections 40a, 40b, respectively, of annular track 40. More specifically, first and second pairs of finger-receiving portions 72, 74 and 76, 78 provide greater access to overtubes 150a, 150b of grasping members 140a, 140b, respectively, when grasping members 140a, 140b are engaged within respective track sections 40a, 40b, thus facilitating the grasping of overtubes 150a, 150b and proximal urging thereof to remove overtubes 150a, 150b from track sections 40a, 40b, respectively.

With continued reference to FIGS. 4-6, the disengagement of hernia repair device 100 from packaging member 10 in preparation for use is described. Initially, the clinician removes protective film 28 from base 20, e.g., by grasping tab member 23a with one hand, grasping the edge of protective film 28 with the other hand, and translating the edge of protective film 28 across base 20 of packaging member 10 until protective film 28 is sufficiently removed from base 20 of packaging member 10 to fully expose hernia repair device 100.

Next, the clinician removes grasping members 140a, 140b from respective track sections 40a, 40b of annular track 40. More specifically, the clinician grasps overtubes 150a, 150b, e.g., adjacent the finger-receiving portions 72 or 74 and finger-receiving portions 76 or 78, respectively, and pulls overtubes 150a, 150b proximally relative to base 20 of packaging member 10 with sufficient urging to move overtubes 150a, 150b beyond knobs 63, 65 of engagement protrusions 62, 64, respectively, to release grasping members 140a, 140b from respective track sections 40a, 40b. The clinician then grasps opposed ends of surgical mesh 110 and translates surgical mesh 110 proximally from central recess 30 of base 20 of packaging member 10 to remove surgical mesh 110 from packaging member 10. Indicia 36, 38 indicate the general positions at which to grasp surgical mesh 110 such that, once grasped, folding of surgical mesh 110 along folding axis "F-F" can be readily achieved, as illustrated by indicia 37 and 39 (FIG. 3). Alternatively or additionally, arrows 53, 55 of indicator protrusions 52, 54, respectively, and/or indicator line 34 may be used to ascertain the location of folding axis "F-F," such that surgical mesh 110 can be grasped accordingly, removed from recessed portion 24 of base 20 of packaging member 10, and folded along folding axis "F-F."

Once hernia repair device 100 has been disengaged and removed from packaging member 10, and since surgical mesh 110 is already being grasped so as to facilitate folding surgical mesh 110 about folding axis "F-F," the clinician may fold surgical mesh 110 about folding axis "F-F" by simply approximating the two grasped ends of surgical mesh 110 relative to one another, as illustrated by indicia 37 and 39 (FIG. 3), thus preparing surgical mesh 110 for insertion into a tissue defect. The folded hernia repair device 100 may then be inserted through the tissue defect. Once inserted through the tissue defect, hernia repair device 100 is oriented such that support member 120 is substantially annularly disposed about the tissue defect with flaps 130 positioned adjacent the distal surface, of tissue surrounding the tissue defect.

In order to position and secure hernia repair device 100 relative to tissue surrounding the tissue defect, the clinician grasps overtubes 150a, 150b and pulls overtubes 150a, 150b proximally, thereby effecting proximal pulling of filament loops 142a, 142b, flaps 130, and surgical mesh 110 such that surgical mesh 110 and support member 120 are brought into approximation with the distal surface of tissue surrounding the tissue defect. Further proximal pulling of overtubes 150a, 150b urges flaps 130 into contact with tissue surrounding the tissue defect. The clinician may secure flaps 130 to the tissue in any suitable fashion, e.g., adhering, tacking, suturing, etc. Thereafter, the clinician may release overtubes 150a, 150b from flaps 130 by cutting filament loops 142a, 142b.

Figure 7:
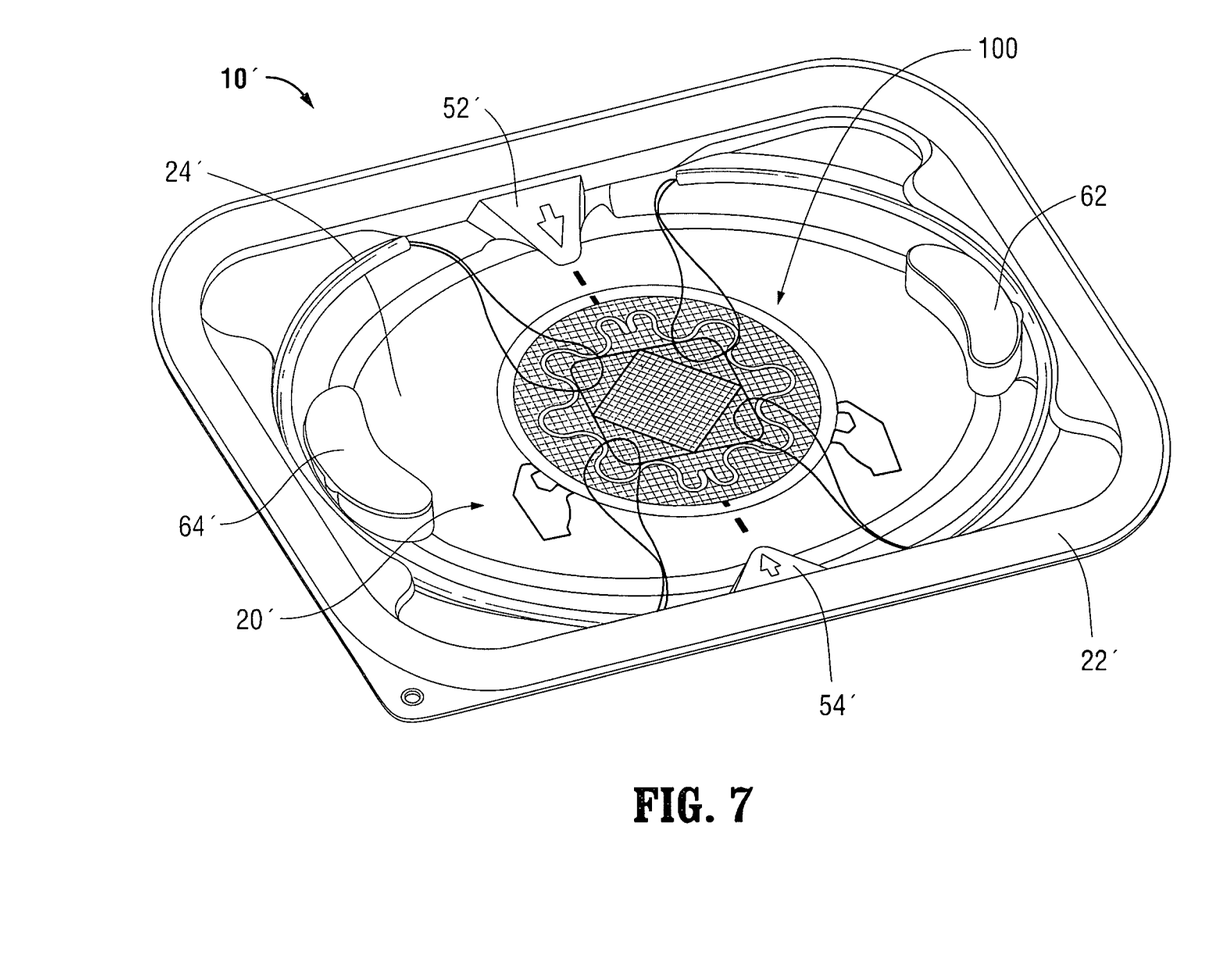
FIG. 7 is a top, perspective view of another packaging member for a hernia repair device provided in accordance with the present disclosure, shown retaining a hernia repair device therein.

Turning to FIG. 7, another embodiment of a packaging member (generally designated by reference numeral 10' provided in accordance with the present disclosure is configured for retaining hernia repair device 100, or any other suitable hernia repair device so as to facilitate the removal of the hernia repair device from packaging member 10' while maintaining proper orientation of the device and inhibiting tangling or damaging the device. Packaging member 10' is similar to packaging member 10 (FIG. 1) and, thus, only the differences between packaging member 10' and packaging member 10 (FIG. 1) will be described to avoid unnecessary repetition.

Continuing with reference to FIG. 7, and with additional reference to FIG. 1, packaging member 10' differs from packaging member 10 in that engagement protrusions 62', 64' of packaging member 10' define rounded, crescent-shaped configurations, whereas engagement protrusions 62, 64 of packaging member 10 define substantially oval-shaped configurations. Packaging member 10' further differs from packaging member 10 in that indicator protrusions 52', 54' of packaging member 10' are sloped or angled from peripheral flange 22' of base 20' down to the floor of recessed portion 24' of base 20', while the top surfaces of indicator protrusions 52, 54 of packaging member 10 are substantially parallel relative to the floor of recessed portion 24 of base 20 and peripheral flange 22 of base 20. It is envisioned that these features be interchanged, e.g., to provide a packaging member including the engagement protrusions of packaging member 10 and the indicator protrusions of packaging member 10' or vice versa. Further, it is envisioned that other suitable configurations of indicator protrusions and/or engagement protrusions may be provided.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A packaging member for a hernia repair device including a surgical mesh and at least one grasping member, the packaging member comprising:
   a central portion configured to receive the surgical mesh;
   at least one recessed track section disposed annularly about the central portion and including an annular cross-section extending therealong, the at least one recessed track section configured to receive the at least one grasping member; and
   a knob extending into the at least one recessed track section, the knob configured to retain the at least one grasping member within the at least one recessed track section.

2. The packaging member according to claim 1, wherein the hernia repair device defines a folding axis, the packaging member further including a pair of indicia indicating a location of the folding axis.

3. The packaging member according to claim 1, wherein the central portion includes a recess configured to receive the surgical mesh.

4. The packaging member according to claim 1, further comprising at least one finger-receiving portion positioned adjacent the at least one recessed track section, the at least one finger-receiving portion configured to facilitate grasping of the at least one grasping member for removal from the packaging member.

5. The packaging member according to claim 1, further comprising a protective film configured for positioning about the packaging member to maintain the hernia repair device in a sterile state.

6. The packaging member according to claim 5, wherein the packaging member further includes a tab configured to facilitate separation of the protective film from the packaging member.

7. The packaging member according to claim 1, further comprising grasping indicia disposed on the central portion, the grasping indicia positioned to indicate grasping positions for grasping the surgical mesh.

8. The packaging member according to claim 1, wherein the hernia repair device includes a pair of opposed grasping members and wherein the at least one recessed track section includes a pair of opposed recessed track sections configured to receive the opposed grasping members.

9. A surgical package, comprising:
   a hernia repair device, including:
   a surgical mesh; and
   first and second grasping members coupled to the surgical mesh; and
   a packaging member for retaining the hernia repair device, the package member including:
   a central portion configured to receive the surgical mesh; and
   first and second opposed recessed track sections disposed annularly about the central portion and including an annular cross-section extending therealong, the first and second opposed recessed track sections configured to receive the first and second grasping members, respectively.

10. The surgical package according to claim 9, wherein the packaging member further includes first and second knobs extending into the first and second track sections, the first and second knobs configured to retain the first and second grasping members within the first and second track sections, respectively.

11. The surgical package according to claim 9, further comprising a protective film configured for positioning about the packaging member to maintain the hernia repair device in a sterile state.

12. The surgical package according to claim 9, wherein the hernia repair device defines a folding axis and wherein the packaging member includes a pair of indicia indicating a location of the folding axis.

13. The surgical package according to claim 9, further comprising grasping indicia disposed on the central portion of the packaging member, the grasping indicia positioned to indicate grasping positions for grasping the surgical mesh.

14. A surgical package, comprising:
   a hernia repair device, including:
   a surgical mesh having first and second support members defining a folding axis therebetween; and
   first and second grasping members coupled to the surgical mesh, the first grasping member disposed on a first side of the folding axis and the second grasping member disposed on a second side of the folding axis; and
   a packaging member for retaining the hernia repair device, the package member including:
   a central portion configured to receive the surgical mesh, the central portion including at least one indicia configured to indicate a location of the folding axis; and
   first and second opposed recessed track sections disposed annularly about the central portion and including an annular cross-section extending therealong, the first and second opposed recessed track sections configured to receive the first and second grasping members, respectively.

15. The surgical package according to claim 14, wherein the packaging member further includes first and second knobs extending into the first and second track sections, the first and second knobs configured to retain the first and second grasping members with the first and second track sections, respectively.

16. The surgical package according to claim 14, wherein the central portion of the packaging member includes a recess configured to receive the surgical mesh.

17. The surgical package according to claim 14, wherein the packaging member further includes at least one finger-receiving portion positioned adjacent the first and second track sections, the at least one finger-receiving portion configured to facilitate grasping of the first and second grasping members for removal from the packaging member.

18. The surgical package according to claim 14, further comprising a protective film configured for positioning about the packaging member to maintain the hernia repair device in a sterile state.

19. The surgical package according to claim 18, wherein the packaging member further includes a tab configured to facilitate separation of the protective film from the packaging member.

20. The surgical package according to claim 14, further comprising grasping indicia disposed on the central portion of the packaging member, the grasping indicia positioned to indicate grasping positions for grasping the surgical mesh.

* * * * *